US00PP08425P

United States Patent [19]

Jessel, Jr.

[11] Patent Number: Plant 8,425

[45] Date of Patent: Oct. 19, 1993

[54] CARNATION PLANT NAMED CFPC CHAPARRAL

[75] Inventor: Walter H. Jessel, Jr., Salinas, Calif.

[73] Assignee: California Florida Plant Co., L.P., Salinas, Calif.

[21] Appl. No.: 950,306

[22] Filed: Sep. 24, 1992

[51] Int. Cl.[5] ..... A01H 5/00

[52] U.S. Cl. ..... Plt./70.2

[58] Field of Search ..... Plt./70.1, 70.2

[56] References Cited

U.S. PATENT DOCUMENTS

P.P. 4,667 3/1981 Jessel, Jr. et al. ..... Plt. 70.2

*Primary Examiner*—Howard J. Locker

*Attorney, Agent, or Firm*—Christie, Parker & Hale

[57] ABSTRACT

A new carnation plant producing sprays of orange picotee red flowers.

1 Drawing Sheet

SUMMARY OF THE INVENTION

The present invention relates to a new and distinct variety of carnation plant which was originated by me in a controlled breeding program by my crossing as seed and pollen parents, two unnamed and unpatented seedlings of my creation, Nos. 871085 and 870708, respectively. The varietal denomination of this new carnation is 'CFPC Chaparral'.

Among the novel characteristics of 'CFPC Chaparral' are (1) production of sprays of orange picotee red with relatively smooth petal edge, (2) more intense orange flower color than 'Lek's Medea' and 'Chiharu' and (3) improved resistance to Rhizoctonia and Sclerotinia.

Asexual reproduction by propagation by side shoot cuttings of the new variety as performed in Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Chaparral.'

BRIEF DESCRIPTION OF THE ILLUSTRATION

The accompanying illustration shows typical specimens of the vegetative growth and flowers in different stages of development of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate from the stated values depending upon varying environmental, seasonal end cultural conditions.

The information provided herein is based on observations of plants grown inside commercial greenhouses at Salinas, Calif. The height of plant and flower and foliage size are established as an average using standard commercial cultural practices.

Name: 'CFPC Chaparral'.

Classification:

*Botanical.*—*Dianthus caryophyllus.*

*Commercial.*—Carnation, spray type.

Parentage:

*Female parent.*—Unnamed seedling (No. 871085).

*Male parent.*—Unnamed seedling (No. 870708).

Plant:

*Height.*—About 31 inches.

*Growth habit.*—Herbaceous, semi-upright.

*Blooming habit.*—Terminal as a spray.

*Blooming season.*—Year round.

*Rooting time.*—About 15-16 days.

*Mutation prone.*—Does not appear to be.

*Disease resistance.*—Not sensitive to water molds, improved resistance to Rhizoctonia and Sclerotinia.

*Breaking action.*—Excellent.

Foliage:

*Color.*—Upper side: Green, near 141A.

*Lower side: Green, near* 141C.

*Size.*—About 7½ inches at base of plant.

*Quantity.*—Numerous.

*Shape.*—Lanceolate.

*Texture.*—Smooth.

*Ribs.*—Central, keeled.

*Arrangement.*—Bi-lateral along stem.

*Stem color.*—Green.

Bud:

*Shape.*—Oval.

*Color.*—Green.

*Length.*—About 1½ inches.

*Diameter.*—About ½ -inch.

Calyx:

*Number of sepals.*—About 5.

*Length.*—About 1-inch.

*Width.*—About ¼-inch.

*Color.*—Outside — near to 143B. Inside — near to 143D.

Bloom:

*Shape.*—Round.

*Size.*—Diameter average: About 2-inches. Depth average: About 1-inch.

*Borne.*—Terminal as a spray.

*Color.*—General tonality: Orange picotee red, (very fine or narrow picotee band, 45B to 45C). Upper side: Near to from 34C to 34D. Lower side: Near to from 34D to 28D. Center: Near to from 34C to 34D. Outer petals: Near to from 34C to 34D.

*Keeping quality.*—Good.

*Fragrance.*—Slight.

Petals:

*Number.*—About 30 to 31.

*Outer petals.*—Length: About $1\frac{3}{8}$ inches. Width: About $\frac{3}{8}$-inch.

*Central petals.*—Length: About $\frac{5}{8}$-inch. Width: About $\frac{3}{4}$-inch.

*Texture.*—Smooth.

*Form.*—Fan shaped.

*Appearance.*—Shiny.

Reproductive organs:

*Stamens.*—Number: About 18. Arrangement: Around the ovary.

Anthers.—Length: About 1/8-inch. Color: Near 161B.

*Filaments.*—Length: About 1-inch. Color: Near 155D.

*Pistil.*—Number: About 2.

Stigma.—Number: About 2. Color: Near 34D.

Ovary.—Shape: Conical. Color: Base — green. Body — green. Apex — tan.

*Fertility.*—Male —good. Female — good.

I claim:

1. A new and distinct variety of carnation plant, substantially as shown and described.

* * * * *

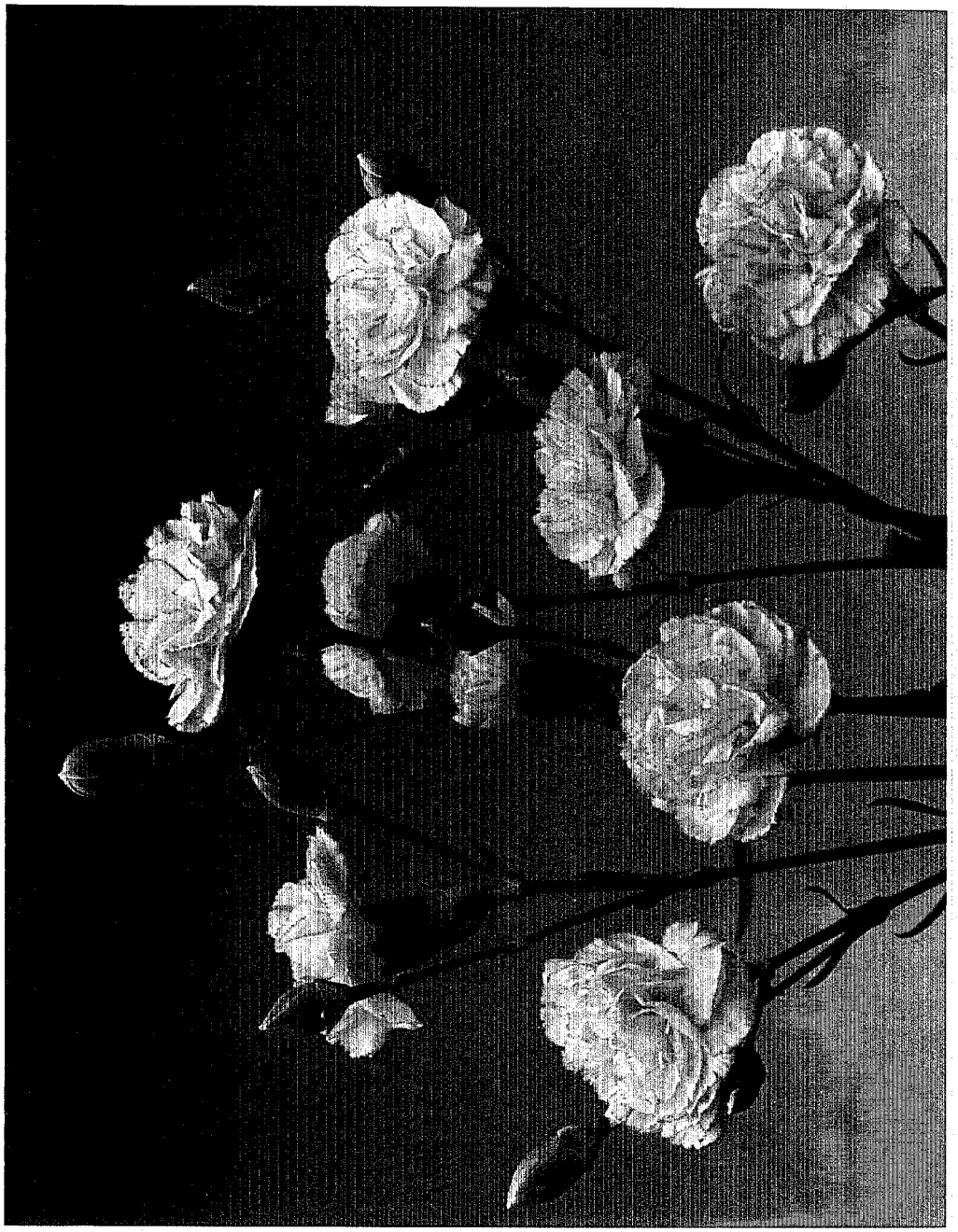

UNITED STATES PATENT AND TRADEMARK OFFICE

CERTIFICATE OF CORRECTION

PATENT NO. : Plant 8,425

DATED : October 19, 1993

INVENTOR(S) : Walter H. Jessel, Jr.

It is certified that error appears in the above-indentified patent and that said Letters Patent is hereby corrected as shown below:

Column 1, line 12, before "with" insert -- flowers --.

Column 1, line 40, after "seasonal" change "end" to -- and --.

Column 3, line 11, change "3/4-inch" to -- 1/2-inch --.

Signed and Sealed this

Twenty-first Day of June, 1994

*Attest:*

Bruce Lehman

BRUCE LEHMAN

*Attesting Officer*

*Commissioner of Patents and Trademarks*